United States Patent [19]

Berger et al.

[11] Patent Number: 4,952,393
[45] Date of Patent: Aug. 28, 1990

[54] ORGAN INFARCT IMAGING WITH TECHNETIUM LABELLED GLUCARATE

[75] Inventors: Harvey J. Berger, Devon, Pa.; Ban A. Khaw, Milton, Mass.; Koon Y. Pak, Bluebell, Pa.; H. William Strauss, Newton Centre, Mass.

[73] Assignee: The General Hospital Corporation, Boston, Mass.

[21] Appl. No.: 254,961

[22] Filed: Oct. 7, 1988

Related U.S. Application Data

[63] Continuation-in-part of Ser. No. 34,003, Apr. 12, 1987.

[51] Int. Cl.$^5$ .................... A61K 49/02; C07F 13/00
[52] U.S. Cl. ............................... 424/1.1; 534/14
[58] Field of Search ................. 424/1.1, 9; 534/14

[56] References Cited

U.S. PATENT DOCUMENTS

| | | | |
|---|---|---|---|
| 4,027,005 | 5/1977 | Adler et al. | 424/1.1 |
| 4,372,941 | 2/1983 | Ryan | 424/1.1 |
| 4,431,626 | 2/1984 | Henze | 424/1.1 |
| 4,666,698 | 5/1987 | Schwarz | 424/1.1 |
| 4,732,974 | 3/1988 | Nicolotti et al. | 424/1.1 X |

OTHER PUBLICATIONS

L. L. Hwang et al., *Int. J. App. Radiat. Isot.*, 36(6): 475–480 (1985).
W. Kieviet, *J. Nucl. Medicine*, 22:703–709 (1981).
C. D. Russell and A. G. Speiser; *J. of Nuclear Medicine*, 21(11):1086–1090 (1980).
W. H. Horner et al., *J. Nuclear of Medicine*, 21:523–528 (1980).
M. K. Dewanjee and H. W. Wahner, *Radiology*, 132:711–716.
T. W. Ryerson et al., *Radiology*, 127:429–432 (1978).
A. J. Roberts et al., *Journal of Surgical Research*, 25:83–91 (1978).
D. R. Alonso et al., *The American Journal of Cardiology*, 42:251–258 (1978).
A. J. Roberts et al., *The Annals of Thoracic Surgery*, 27:42–48 (1978).
J. G. Jacobstein et al., *Journal of Nuclear Medicine*, 18(5):413–418 (1977).
Z. D. Grossman et al., *Journal of Nuclear Medicine*, 18(1):51–56 (1977).
B. L. Holman et al., *Radiology*, 121:427–430 (1976).
H. R. Schelbert et al., *Circulation Research*, 39(6):860–868 (1976).
N. Adler et al., *Journal of Nuclear Medicine*, 17(3):203–207 (1976).
D. J. Rossman et al., *Journal of Nuclear Medicine*, 16(11):980–985 (1975).
F. G. Zweiman et al., *Journal of Nuclear Medicine*, 16(11):975–979 (1975).
D. J. Rossman et al., *Journal of Nuclear Medicine*, 16(10):865–878 (1975).

*Primary Examiner*—John S. Maples
*Attorney, Agent, or Firm*—Hamilton, Brook, Smith & Reynolds

[57] ABSTRACT

Method using technetium-99m imaging agents for the study, detection or diagnosis of ischemic, infarcted or diseased tissue. The imaging agents comprise a complex of technetium-99 m and glucarate.

4 Claims, 1 Drawing Sheet

ORGAN INFARCT IMAGING WITH TECHNETIUM LABELLED GLUCARATE

RELATED APPLICATIONS

This application is a continuation-in-part of U.S. Pat. application Ser. No. 034,003, filed Apr. 2, 1987 entitled "Methods For Labeling Antibodies With A Metal Ion" by Koon Yan Pak, Richard T. Dean and Jeffrey A. Mattis.

BACKGROUND OF THE INVENTION

Radiolabeled compounds have long been used in diagnostic and therapeutic procedures. Some radio metals have superior properties for use in these procedures. Technetium-99m (Tc-99m) is an ideal radionuclide for scintigraphic imaging because of its radioactive decay properties. It has a single photon energy of 140 keV, a half life of about 6 hours, and it is readily available from a $^{99}$Mo-$^{99m}$Tc generator.

There is a large family of polyhydric complexes of technetium, with and without carboxylic acid groups, which differ widely in stability. Hwang, et al., *Intl. J. of Appl. Radiat. Isot.*, 36 (6): 475–480 (1975). Hydroxycarboxylates tend to form soluble complexes with transition metals. Technetium (Tc) complexes of these compounds have been used for the nuclear imaging of kidneys, brain, myocardial infarcts and tumors. Russell and Speiser, *J. Nucl. Med.*, 21: 1086–1090 (1980). $^{99m}$Tc-D-glucoheptonate is the most widely used imaging agent. It has been used for brain and kidney imaging. Waxman, et al., *J. Nucl. Med.*, 17: 345–348 (1976) and Arnold, et al., *J. Nucl. Med.*, 16: 357–367 (1975). See also, Adler, et al., U.S. Pat. No. 4,027,005. However, $^{99m}$Tc-D-glucoheptonate has been less successful as an imaging agent for myocardial infarct. Rossman, et al., *J. Nucl. Med.*, 16: 980–985 (1975).

Much effort has been directed toward evaluating the usefulness of various radionuclides and radiopharmaceuticals for imaging myocardial tissue. Since the widespread use of surgery to treat coronary artery disease, accurate detection of perioperative myocardial infarction has become critical for the objective evaluation of operation results, especially of surgical patients who are at a high risk for myocardial necrosis. Perioperative infarction has been cited as a major cause of operative death and postoperative cardiac failure. Roberts, et al., *J. of Surgical Research*, 25:83–91 (1978). Myocardial imaging agents offer an effective, non-invasive method to detect myocardial infarct in these patients.

SUMMARY OF THE INVENTION

This invention pertains to a radionuclide imaging agent which is a complex of Tc-99m and a carbohydrate ligand, and a method for detecting ischemic, infarcted or diseased tissue, using the complex. The carbohydrate component is a compound having the general formula:

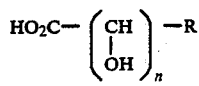

wherein n can be an integer from 1 to 10 inclusive; R can be —CO$_2$H, —PO$_3$H$_2$, —SO$_3$H, —N$^+$R'$_3$, —CHO, or an alkyl group having between one and five carbon atoms. The alkyl groups may be substituted, provided the substituents are not hydroxyl groups. R' can be a substituted or unsubstituted alkyl group having from 1 to 5 carbon atoms. The carbohydrate component can be a salt, such as an alkali metal salt, of the carboxylate form of the compound.

The preferred complex is Tc-99m-glucarate. Tc-99m-glucarate is a biologically acceptable imaging agent for scintigraphic imaging of ischemic, infarcted or diseased tissue in the brain, kidney, heart or other organs.

In general, the method of detecting ischemic, infarcted or diseased tissue using the Tc-99m-carbohydrate complex comprises: forming an aqueous mixture of TC-99m in an oxidized form, such as the pertechnetate ion, with a reducing agent and the carbohydrate ligand of the formula above, such as glucaric acid, to provide a TC-99m-carbohydrate complex, administering the Tc-99m-carbohydrate complex to the subject, allowing the Tc-99m-carbohydrate to localize at the site of ischemia, infarct or disease, and scanning the subject with a gamma camera to obtain an image of the diseased tissue.

The carbohydrate ligands employed in the method of this invention are capable of complexing technetium-99m in stable form without the formation of a significant amount of technetium colloids. For example, radiolabeled glucarate is stable in solution and, in addition, the labeling method can be performed rapidly (can be completed in less than one hour). The method can be performed at room temperature, at a pH between about 5–9. The labeled product does not require purification prior to administration.

DETAILED DESCRIPTION OF THE INVENTION

Figure 1:
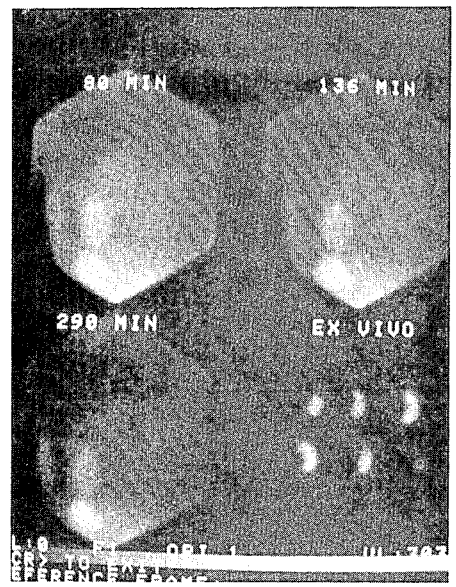
FIG. 1 shows scintigraphic images taken at 80, 136 and 290 minutes after the injection of Tc-99m-glucarate into a dog with acute myocardial infarct. The area of myocardial necrosis is clearly visible at 80 minutes with minimum blood activity.

The Tc-99m-carbohydrate complex of this invention can be made by reacting Tc-99m in an oxidized state with a carbohydrate or a carbohydrate salt in the presence of a reducing agent under conditions which allow formation of a stable complex between Tc-99m in a reduced state (e.g., IV or V valence state) and the carbohydrate ligand. The preferred carbohydrate ligands are carbohydrates having the general formula:

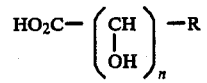

or salts thereof, wherein n can be an integer from 1 to 10 inclusive; and R can be —CO$_2$H, —PO$_3$H$_2$, —SO$_3$H, —N$^+$R'$_3$, —CHO, or a substituted or unsubstituted alkyl group having between one and five carbon atoms, provided that the substituents are not hydroxyl groups. R' can be an substituted or unsubstituted alkyl group having from 1 to 5 carbon atoms. The alkyl substituents can include amine groups or halogens, for example. The carbohydrate salts can be alkali metal salts (e.g., sodium or potassium). The ligand should be selected so that it complexes quickly with Tc-99m to form a stable, biologically acceptable complex.

Particularly preferred ligands are glucaric acid (also known as saccharic acid), or salts of glucaric acid, such as, for example, potassium glucarate. Glucaric acid complexes with Tc-99m quickly to form a stable Tc-99m-glucarate complex. Tc-99m labeled glucarate is a biologically acceptable imaging agent.

The source of Tc-99m should preferably be water soluble. Preferred sources are alkali and alkaline earth metal salts of pertechnetate (TcO$_4^-$) such as, for example, sodium pertechnetate. Tc-99m is most preferably obtained in the form of fresh sodium pertechnetate from a sterile Tc-99m generator (e.g., from a conventional $^{99}$Mo/$^{99m}$Tc generator). Any other source of physiologically acceptable Tc-99m may be used.

Reducing agents must be physiologically acceptable and effective for reducing technetium-99m from its oxidized state to the IV or V oxidation state. Examples of suitable reducing agents are stannous chloride, stannous fluoride, stannous tartarate, and sodium dithionite. The preferred agents are stannous reducing agents, such as stannous chloride and stannous fluoride. The most preferred agent is stannous chloride.

The amount of reducing agent used is the amount necessary to reduce the technetium to provide for binding to the ligand in a reduced state. In a preferred mode, stannous chloride (SnCl$_2$) is the reducing agent, and the concentration may range between about 1–1000 ug/ml, preferably between about 30–500 ug/ml. The amount of the ligand may range from about 0.5 mg/ml up to the amount maximally soluble in the medium. In a preferred embodiment, where the ligand is glucarate, the amount of glucarate (as potassium glucarate) may range from about 0.5 mg/ml up to the amount maximally soluble in the medium. Preferred amounts of glucarate range from between about 5–30 mg/ml.

Tc-99m in the form of pertechnetate can be used in amounts up to about 50 mCi/ml, preferably between about 25–50 mCi/ml.

The reaction between the pertechnetate ion and ligand is preferably carried out in aqueous solution at a pH at which the Tc-99m-carbohydrate complex is stable. Normally the pH for the reaction will be physiological pH, between about 5 and 9, the preferred pH being between about 6 and 8. The metal ion-ligand complex is incubated, preferably at a temperature from about 20° C. to about 60° C., most preferably from about 20° C. to about 37° C., for a sufficient amount of time for transfer of the metal ion to the ligand complex. Generally, less than one hour is sufficient to complete the reaction under these conditions.

In a preferred embodiment, aqueous sodium 99m pertechnetate is mixed with an aqueous solution of stannous reducing agent and glucaric acid (or salt thereof) to form Tc-99m-glucarate. The entire procedure can be conducted in less than one hour at room temperature and at a pH of between about 5–9. Under these conditions, an essentially complete transfer of technetium-99m can be obtained. The various reagents used in the method, and the parameters of the method are discussed in detail below.

In the present method, Tc-99m labeled carbohydrate can be used in scintigraphy for the imaging of diseased tissue, particularly ischemic and infarcted tissue. The Tc-99m-glucarate complex is particulary effective for imaging myocardial ischemia or infarct and cerebral infarct. Tc-99m-glucarate is unique in its ability to obtain images in the brain because it can diffuse across the blood-brain barrier. Although not wishing to be bound by theory, it is believed that glucarate functions as a glucose analog, in a manner similar to $^{18}$F-fluoro deoxyglucose (PET agent), and thereby is capable of rapid stroke imaging. On the other hand, glucoheptonate imaging agents localize to stroke by virtue of altered blood-brain barrier and have slower diffusion/uptake into stroke.

In the present method, an effective imaging amount of Tc-99m-carbohydrate preferably Tc-99m-glucarate, is injected parenterally (preferably intraveneously) into a subject. The dosage may vary, depending upon the area and tissue to be imaged, the age and condition of the patient and other factors which a skilled practitioner would consider. After injection, sufficient time is allowed for the Tc-99m-carbohydrate complex to accumulate at the site of the diseased tissue. For example, Tc-99m-glucarate localizes to provide an avid myocardial infarct image in dogs within one and a half hours, and a cerebral infarct image in rats within one hour. Thus, it is believed that Tc-99m-glucarate is diagnostically applicable within one to two hours of the infarct or ischemic event in the subject. The subject can then be scanned with a gamma camera to detect the gamma emmission of the Tc-99m, to thereby obtain an image of the diseased area. In this way, the ischemic tissue or infarction can be localized and its size can be determined.

The reagents for performing the labeling method can be assembled in kits for convenient performance of the method in the clinic. At minimum, a kit for radiolabeling the ligand with the radiometal can consist of a sealed and sterile vial containing reducing agent (preferably stannous ions) and the carbohydrate ligand (preferably glucaric acid) in aqueous solution. The pertechnetate ion is added to the vial containing the reducing agent and the ligand. The contents are then mixed and incubated for a time sufficient to effect labeling of the ligand. The radiolabeled ligand can then be used immediately without purification.

The invention is further illustrated by the following exemplification:

EXEMPLIFICATION

Example 1

Preparation of $^{99m}$Tc-Glucarate

Monopotassium glucarate (25 mg) was dissolved in 0.2M bicarbonate (1.0 ml) at pH 8.0. To 500 ul of glucarate solution, 40 ul of stannous chloride (2.5 mg/ml) in 0.1M acetic acid was added, followed by 500 ul of $^{99m}$Tc generator eluate (60 mCi). The resulting solution was allowed to stand for 5 minutes at room temperature, and then analyzed for radiochemical purity by paper chromatography (Whatman 3MM, 60% CH$_3$CN:40% H$_2$O)

Example 2

The Effect of Glucarate Concentration on the Formation of $^{99m}$TC-Glucarate $^{99m}$Tc-glucarate was prepared as described in Example 1 using different concentrations of potassium glucarate (0.09–12.25 mg/ml). The products were analyzed by paper chromatography (Whatman 3MM, 60% $CH_3CN$:40%$H_2O$; $^{99m}TcO_4^-$ $Rf$=1.0, $^{99m}$Tc-glucarate, Rf=0.4; $^{99m}TcO_2 \times H_2O$, Rf=0). The data in Table 1 show that a concentration of 6 mg/ml potassium glucarate in 0.2M bicarbonate is sufficient to completely stabilize the reduced technetium.

TABLE 1

Percent of $^{99m}TcO_2$ and $^{99m}$Tc-Glucarate After Incubation at Room Temperature for 1 Hr. at Various Concentrations of Glucaric Acid as Analyzed by Paper Chromatography.

| Glucaric Acid (mg/ml) | % $^{99m}TcO2$ | % $^{99m}$Tc-Glucarate |
|---|---|---|
| 12.25 | .0 | 100.0 |
| 6.12 | .0 | 100.0 |
| 3.06 | 11.5 | 88.5 |
| 1.53 | 19.5 | 80.5 |
| 0.76 | 24.4 | 75.6 |
| 0.38 | 30.0 | 70.0 |
| 0.19 | 41.0 | 59.0 |
| 0.09 | 57.0 | 43.0 |

Example 3

Stability of $^{99m}$Tc-Glucarate

Samples of $^{99m}$-Tc-glucarate prepared as described in Example 1 from 6 and 12 mg/ml potassium glucarate were analyzed over a period of 7 hours. The results shown in Table 2, indicate that the preparation made from 12 mg/ml glucarate was more stable, and was stable for a period of about 2 hours.

TABLE 2

Stability of $^{99m}$Tc-Glucarate at room temperature

| Time Hours | 6.12 mg/ml | | 12.24 mg/ml | |
|---|---|---|---|---|
| | % Tc-GLUC | % TcO4− | % Tc-GLUC | % TcO4− |
| 1 | 95 | 5 | 95 | 5 |
| 3 | 76 | 24 | 82 | 18 |
| 5 | 45 | 55 | 62 | 38 |
| 7 | 36 | 64 | 60 | 40 |

Example 4

Biodistribution of $^{99m}$Tc-Glucarate in Various Organs in Balb/c Mice

Biodistribution studies were carried out in Balb/c mice. The mice (3 mice per group) were injected intravenously with 100 uCi of technetium-labeled D-glucarate. Groups of mice were sacrificed 1,4 and 8 hours after injection, and the organs removed, weighed and counted.

Table 3 shows the uptake of Tc-99m-glucarate by various organs at times ranging from 1-24 hours.

TABLE 3

Biodistribution In % Injected Dose Per Gram Of $^{99m}$Technetium Labeled D-Glucarate At 1, 4, 8 and 24 Hours Post Injection In Mice

| | 1 Hour | 4 Hours | 8 Hours | 24 Hours |
|---|---|---|---|---|
| Blood | 1.72 ± 0.43 | 1.26 ± 0.22 | 0.90 ± 0.29 | 0.56 ± 0.09 |
| Spleen | 0.44 ± 0.76 | N/A | N/A | N/A |
| Stomach | 0.935 ± 0.54 | 3.49 ± 5.10 | 1.13 ± 0.98 | 0.39 ± 0.34 |
| Intestine | 2.90 ± 1.12 | 2.02 ± 0.90 | 0.89 ± 0.46 | 0.58 ± 0.36 |
| Kidneys | 24.3 ± 4.15 | 28.50 ± 0.75 | 19.20 ± 5.00 | 8.4 ± 1.74 |

TABLE 3-continued

Biodistribution In % Injected Dose Per Gram Of $^{99m}$Technetium Labeled D-Glucarate At 1, 4, 8 and 24 Hours Post Injection In Mice

| | 1 Hour | 4 Hours | 8 Hours | 24 Hours |
|---|---|---|---|---|
| Liver | 1.54 ± 0.51 | 1.49 ± 0.08 | 1.03 ± 0.18 | 0.42 ± 0.05 |
| Lungs | 3.90 ± 1.80 | 3.43 ± 1.35 | 1.95 ± 1.04 | 1.52 ± 1.02 |
| Heart | 0.63 ± 1.10 | 0.75 ± 1.30 | 0.30 ± 0.52 | N/A |
| Muscle | 0.32 ± 0.20 | 2.31 ± 2.98 | 0.59 ± 0.82 | 0.68 ± 1.00 |

N/A = Not Available

Example 5

Detection of Myocardial Infarct in the Dog $^{99m}$Tc-glucarate was injected into acute myocardial infarct dog.

Mongrel dogs (n=3) were anesthetized with intravenous pentobartitol (30 mg/kg), and respiration maintained on a Harvard respirator. Left thoractomy was performed, the heart suspended in a pericardial cradle and a segment of the left anterior descending coronary artery (LAD) approximately two thirds the distance from the apex to the base was dissected free. The LAD was then occluded with a silk ligature. After three hours of LAD occlusion, the occlusive ligature was removed and reperfusion was established. At 15 minutes of reperfusion, 200 uCi of indium labeled R11D10 Fab-DTPA (Centocor, Inc.) was injected, and 30 seconds later, 10 mCi of technetium labeled glucarate was injected. Serial imaging with a gamma camera was initiated immediately upon tracer administration.

Tc-99m images were obtained using 140 KeV photopeak with a 20% window and In-111 images were attained using 247 KeV photopeak with a 20% window. After 5 hours of in vivo imaging sessions, the dogs were sacrificed by pentobarbital overdose. Then, the cardiac tissue was stained with an intravenous triphenyltetrazolium chloride infusion. The heart was excised, washed with cold water, and imaged as a whole excised heart; and also as heart slices cut parallel to the atrioventricular groove in four slices after overnight storage at 4° C. Each slice was then divided into eight equal pieces and each piece subdivided into epicardial and endocardial samples, weighed and then counted in a gamma well counter (LKB Compu Gamma counter) for distribution of the various radioisotopes. Counts from regions of interest were obtained from 127–140 KeV for Tc-99m, and 174–247 KeV for In-111. Blood samples from the contralateral vein were obtained at 1, 2, 3, 4, 5, 10, 15, 20, 30, 45, 60, and 75 minutes. Blood clearance was determined by using the 1 minute blood sample at 100%. At the time of sacrifice, tissue samples from the liver, lungs, kidneys, spleen, and skeletal muscles were also obtained.

Scintigraphic images taken at 80, 136 and 290 minutes after injection showed that the area of acute myocardial necrosis is clearly visualized at 80 minutes with minimum blood pool activity. The results shown in the Figure. Distinct uptake of $^{99m}$Tc-glucarate is clearly shown in the area of myocardial infarction of the heart slices.

Example 6

Detection of Cerebral Infarct in the Rat

Tc-99m-glucarate was used to visualize cerebral infarct regions in the rat brain.

Experimental cerebral infarcts were created in 28 Sprague-Dawley CD rats (Charles River Laboratories) by injection of thrombin-generated thrombi into an isolated carotid artery. About 1.5-2.0 mCi of Tc-99m-glucarate were injected intravenously into the rats at 1, 3, 5 and 24 hours after release of the thrombi. Imaging was performed 1.5-2.0 hours later utilizing a gamma camera having a 3 mm diameter pin hole collimator. T1-201 diethyldithiocarbamate (DDC) at a concentration of 0.6 mCi was used in each animal as a perfusion deficit marker. The gamma images obtained were analyzed by computer planimetry. Ratios of count densities in infarct regions and normal brain regions were calculated. Rats with ratios of T1-201 DDC activity in infarct:normal brain tissues (n=25) of less than 1:1 were analyzed for Tc-99m-glucarate localization ratios. Duration of cerebral injury did not appear to affect localization of Tc-99m-glucarate. Ratios of Tc-99m-glucarate activity in stroke regions to normal cerebral regions were maximal in all stroke animals. The results are shown in Table 4:

TABLE 4

| | Localization of $^{99m}$Tc-glucarate in Cerebral Infarct Rats | |
|---|---|---|
| Injection Time After Infarct (hours) | Tc-99m-glucarate Activity (mean +/− SD$^a$) | DDC Activity (mean +/− SD$^a$) |
| 1 | 2.98 +/− 0.7 | 0.3 +/− 0.1 |
| 3 | 4.1 +/− 1.7 | 0.3 +/− 0.3 |
| 5 | 4.1 +/− 2.4 | 0.4 +/− 0.2 |
| 24 | 4.8 +/− 1.9 | 0.3 +/− 0.2 |

$^a$SD = standard deviation

Figure 2:
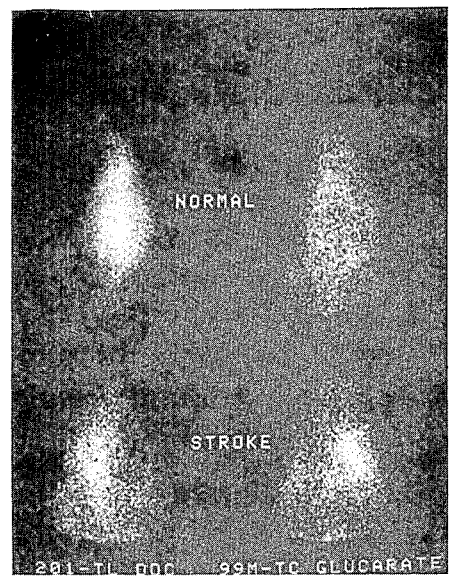
FIG. 2 shows scintigraphic images of a normal rat brain and a rat brain which exhibits a 24-hour-old stroke. The images were taken at 90 minutes after injection of diethyl dithiocarbamate (left side) and Tc-99m-glucarate (right side) to the rats.

All cerebral infarct regions were visualized by gamma scintigraphy with Tc-99m-glucarate, as shown in FIG. 2. Additionally, this study established that $^{99m}$Tc-glucarate accumulation in stroke is more rapid and intense than $^{99m}$Tc-glucoheptonate.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of obtaining an image of a myocardial infarct in a subject, comprising the steps of:
   a. injecting parenterally an effective imaging amount of $^{99m}$Tc-glucarate into the subject;
   b. allowing the $^{99m}$Tc-glucarate to localize at the site of the myocardial infarct; and
   c. scanning the subject with a gamma camera to obtain an image of the myocardial infarct.

2. A method of claim 1 wherein $^{99m}$Tc-glucarate is administered intravenously.

3. A method of obtaining an image of a cerebral infarct in a subject, comprising the steps of:
   a. injecting parenterally an effective imaging amount of $^{99m}$Tc-glucarate into the subject;
   b. allowing the $^{99m}$Tc-glucarate to localize at the site of the cerebral infarct; and
   c. scanning the subject with a gamma camera to obtain an image of the cerebral infarct.

4. A method of claim 3, wherein $^{99m}$Tc-glucarate is administered intravenously.

* * * * *

UNITED STATES PATENT AND TRADEMARK OFFICE
CERTIFICATE OF CORRECTION

PATENT NO. : 4,952,393

DATED : August 28, 1990

INVENTOR(S) : Harvey J. Berger, Ban A. Khaw, Koon Y. Pak and H. William Strauss

It is certified that error appears in the above—identified patent and that said Letters Patent is hereby corrected as shown below:

on the title page: Item [21]
The Assignees should be:
The General Hospital Corporation, Boston, MA
and, Centocor, Inc., Malvern, PA.

Signed and Sealed this

Twenty-fourth Day of December, 1991

Attest:

HARRY F. MANBECK, JR.

*Attesting Officer*      *Commissioner of Patents and Trademarks*